United States Patent [19]
Sato et al.

[11] Patent Number: 5,354,899
[45] Date of Patent: Oct. 11, 1994

[54] PRODUCTION PROCESS OF 1,4,5,8-NAPHTHALENE TETRACARBOXYLIC ACID

[75] Inventors: Toshio Sato; Ikuo Ito; Kyoichi Takeda, all of Kashima, Japan

[73] Assignee: Sumikin Chemical Co., Tokyo, Japan

[21] Appl. No.: 72,242

[22] Filed: Jun. 4, 1993

[30] Foreign Application Priority Data

Jun. 5, 1992 [JP] Japan .................... 4-171771

[51] Int. Cl.$^5$ ............................ C07C 63/48
[52] U.S. Cl. ................................. 562/488
[58] Field of Search ......................... 562/488

*Primary Examiner*—Jose' G. Dees
*Assistant Examiner*—Joseph Conrad
*Attorney, Agent, or Firm*—Harris Beach & Wilcox

[57] ABSTRACT

There is disclosed a mass production process of 1,4,5,8-naphthalene tetracarboxylic acid with high collection efficiency. In the presence of an alkaline metallic catalyst, 1,3-butadiene was added to the ethyl radicals of ethyl-p-xylene, and cyclized to 1,4,5,8-tetramethyl-1,2,3,4-tetrahydronaphthalene which was further dehydrogenated and oxidized to obtain 1,4,5,8-naphthalene tetracarboxylic acid, so that a constant supply of inexpensive 1,4,5,8-naphthalene tetracarboxylic acid can be achieved as an intermediate raw material for dye, pigment, resins, or the like.

12 Claims, 3 Drawing Sheets

PRODUCTION PROCESS OF 1,4,5,8-NAPHTHALENE TETRACARBOXYLIC ACID

BACKGROUND OF THE INVENTION

This invention relates to a novel process for producing a 1,4,5,8-naphthalene tetracarboxylic acid which is a well-known intermediate product for dye, pigment, resins and the like.

In the prior art, 1,4,5,8-naphthalene tetracarboxylic acid (hereinafter referred to as merely "NTCA") has been produced by the halogenation of pyrene which can be produced from a coal tar and by a two-step oxidation with reagents (Ullmann's Encyclopedia of Industrial Chemistry, Vol.A5, p.249). In an alternative method, NTCA has been conventionally synthesized by following steps: using 1,2 dihydroacenaphthylene obtained from coal tar as a starting raw material: adding acyl radicals such as carbon to the 5,6 position: and then by hydrolyzing or oxidizing the result.

A drawback of the halogenation of pyrene and the two-step oxidation with reagent is the difficulty of obtaining pyrene as a raw material. Besides these processes consume a large amount of acid and alkali. Other technical problems include poor yield, and high cost of 1,2-dihydroacenaphthalene as a starting raw substance in the synthesis.

OBJECTS AND SUMMARY OF THE INVENTION

Accordingly, it is an objective of the present invention to provide a novel method for the mass-producttion of NTCA at low cost by using petrochemicals which are readily available in quantity as a starting material, thereby overcoming the shortcomings of the prior art.

As a result of continuous and diligent research and experimentation, the inventors have found a method of NTCA production in which 1,3 butadiene is added to ethyl-p-xylene, and then subjected to cyclization to form 1,4,5,8-tetramethyl-1,2,3,4-tetrahydronaphthalene (hereinafter "TMT"), followed by dehydrogenation and oxidation.

Namely, according to the present invention, 1,3 butadiene is added to ethyl-p-xylene in the presence of an alkaline metal catalyst, and cyclize to form TMT, which further dehydrogenated and oxidized.

Ethyl-p-xylene, as a starting raw material in the present invention, can be easily obtained through nucleophilic ethylation by the reaction of ethylene with p-xylene, or from halogenated ethylene, or by transalkylation of these substances.

The addition reaction of 1,3 butadiene to the ethyl radicals in ethyl-p-xylene is similar to the known addition of olefin to the alkyl radicals of an alkyl aromatic hydrocarbon which has a benzyl hydrogen. Since this addition reaction is achieved by anions, any chemicals which are able to generate active species can react as catalysts. In general, alkaline metals such as sodium, potassium or cesium can be used as a single, alloys or organometallic compounds. In other words, as an alkaline metal catalyst, any catalysts can be used if they are effective as an anion addition catalyst.

If polycyclic aromatics, especially of anthracene, naphthalene, biphenyl, phenanthrene, pyrene or alkyl derivatives thereof are utilized as a promoter, the selectivity can be enhanced. Hence, the adducts which were previously formed by alkaline metal and polycyclic, polynucleic aromatics can also be employed.

The addition reaction of 1,3-butadiene to the aforementioned ethyl radicals of ethyl-p-xylene not only contributes to an improvement in the operation by co-existing with the chain or cyclic ether compounds while dissolving the catalyst, but also enhances selectivity as well as remarkably reducing the amount of catalyst required for the process. Therefore the process is extremely effective. Tetrahydrofuran is an especially effective compound for the ether compounds.

In general, for the addition reaction of 1,3 butadiene to the ethyl radicals of ethyl-p-xylene, regardless of the manner of reactions and order of addition, butadiene is normally supplied in a liquid or gaseous phase either under reduced pressure, at atmospheric pressure, or under excess pressure. The addition reaction can be achieved by a batch process, semi-batch process, or a continuous process.

If the reaction temperature for an addition reaction is low, the reaction rate is slow, but if the reaction temperature is too high, selectivity will be reduced. An optimum reaction temperature generally lies in a range from room temperature up to 100° C. However, there are some cases in which the addition reaction is operated above 100° C., depending upon the type of catalyst used.

Although a solvent can be employed for the addition reaction, it is advantageous to use the ether group solvent for the reasons discussed above. The amount of alkaline metal catalyst used depends greatly upon the use or nonuse of the promoter or tetrahydrofuran. In a case when 2–30 mol % of tetrahydrofuran in the ethyl-p-xylene is not used, it would be suitable to use 0.5–15 mol % of alkaline metal catalyst with ethyl-p-xylene. If the alkaline metal catalyst is added excessively, the reaction will proceed without complication, but such practice is uneconomical. If sufficient catalyst is not added, selectivity might be reduced.

The amount of promoter used may be 0.05–0.5 mol % for each mol of catalyst used. Addition of excessive promoter will not cause any problems, but insufficient promoter may decrease the effect. Regarding the amount of tetrahydrofuran used, it is preferable to choose 0.01–100 times more than the amount of the ethyl-p-xylene. More preferably it would be 0.1–10 times, and 0.2–2 times is the most preferable ratio. Addition of excessive tetrahydrofuran will not adversely affect the chemical reaction, but would reduce productivity. On the other hand, the effect might be reduced if the amount is not sufficient. If the amount of 1,3-butadiene is excessive, di-adduct will easily be formed; on the other hand, if too little, productivity will drop. Therefore, an appropriate ratio should be approximately 0.3–0.7 mol % per mol of ethyl-p-xylene. In the addition reaction, the ethyl-p-xylene and 1,3-butadiene, after the 1:1 adduct is synthesized, 5-(p-xylyl)-hexene is separated by, for example, a distillation with or without the decomposition of the catalysts. The position of the unsaturated bond of the 5-(p-xylyl)-hexene may be at the 2-position. In a case where tetrahydrofuran or solvent are used, they can be collected at this stage of the reaction for recycling.

It is unnecessary to require highly pure 5-(p-xylyl)-hexene for the next stage as the cyclization reaction. 5-(p-xylyl)-hexene including unreacted ethyl-p-hexene, solvent, or tetrahydrofuran can be used. The catalyst for the cyclization process can be used an alkylation catalyst of aromatics, including aluminum chloride anhydrous, boron trifluoride, hydrogen fluoride, phosphoric acid, sulfuric acid, or solid acids such as silica-alumina. However, since TMT—itself a cyclization reaction product—possesses strain energy, more severe conditions are required than for ordinary reactions. According to the results obtained by the present inventors, sulfuric acid or aromatic sulfuric acid will be suitable as the cyclization catalyst. Even using this catalyst, a reaction temperature ranging from 120° to 250° C. is required. Since the solvent or tetrahydrofuran has a low boiling temperature, it will evaporate at the aforementioned temperature range, requiring the evaporated gas to be removed from the reaction system under atmospheric pressure. The sulfuric acid has a polymerizing function, and an aromatic sulfuric acid should be preferably chosen as the catalyst.

If the added amount of the cyclization catalyst ranges from 0.5 to 20% of 5-(p-xylyl)-hexene and can be in the reaction mixture along with the solvent, the cyclization reaction can proceed almost quantitatively. After the cyclization reaction is completed, the TMT as a reaction product is separated by distillation or the like, and supplied to the dehydrogenation reaction.

The dehydrogenation reaction of the TMT can be performed by, in principle, a dehydrogenatic aromatization method for the cyclohexane, cyclohexene, tetrahydronaphthalene, or the like. However, 1,4,5,8-tetramethylnaphthalene as a reaction product is a highly-strained compound having methyl radicals at 1,8- and 4,5-peri-positions, so that it is very difficult to perform the dehydrogenation reaction from the thermodynamic point of view. Hence, it is apparent that the more active catalyst and more severe conditions are needed for the reaction.

The catalyst used for the dehydrogenation reaction can be any catalysts containing noble metals, particularly palladium or platinum. They are supplied for use after being supported with the alumina or active carbon.

The TMT used for the dehydrogenation process is not required to be highly pure if a catalyst poison is not included. A concentration ranging from 60 to 80% will be satisfactory.

The dehydrogenation reaction can be achieved under either reduced pressure, atmospheric pressure, or greater than atmospheric pressure, and may proceed as a batch process, semi-batch process, or continuous process, in either gaseous or liquid phase. In a case when the dehydrogenation process is conducted in the gaseous phase, the catalyst in which platinum or palladium is supported with the active carbon or alumina is employed at above the boiling point of TMT. Under such conditions, the cyclization and dehydrogenation of 5-(p-xylyl)-hexene can be proceeded simultaneously.

It is necessary that the reaction temperature for the dehydrogenation reaction is relatively high, ranging from 150° to 350° C. even in the liquid phase. In this case, including a hydrogen acceptor such as an aromatic nitro compound will provide better results.

Although a solvent is not required for the dehydrogenation reaction operated in the liquid phase, if one is used, a polar solvent would be preferable.

In the dehydrogenation reaction, both 1,4,5,8-tetramethylnaphthalene and 5,6-dimethyl-1,2-dihydroacenaphthylene are produced. Although the ratio between these products depends upon the type of the used catalyst and reaction conditions, this presents no problems because both compounds are oxidized to NTCA.

Separation of the dehydrogenation reaction product from the unreacted TMT can be achieved by well known separation techniques including cooling precipitation, recrystallization, or distillation.

The yield can be became higher by recycling the unreacted TMT which is separated and collected for reuse in the dehydrogenation process.

Side reactions during the dehydrogenation reaction are negligible, and 1,4,5,8-tetramethylnaphthalene and 5,6-dimethyl-1,2-dihydroacenaphthylene can be obtained at a high yield with respect to the consumed amount of TMT.

Oxidation of the 1,4,5,8-tetramethylnaphthalene and 5,6-dimethyl-1,2-dihydroacenaphthylene, both of which are reaction products of the dehydrogenation reaction, can be performed by either liquid phase air oxidation, liquid phase oxidation with reagent, or gaseous phase oxidation. For example, in the case of liquid phase air oxidation, a low molecular weight fatty acid such as acetic acid, an anhydrous low molecular weight fatty acid alone, or its mixture is employed as a solvent. The oxidation is then performed at a reaction temperature ranging from 100° to 220° C. by using one or more than two of a catalyst group comprising cobalt, manganese, copper, cerium, palladium, ruthenium, or the like. If bromine is added to the catalyst system, the reaction rate as well as the yield will be remarkably enhanced. Furthermore, coexisting alkaline metals such as sodium, potassium or the like will become higher the yield.

Moreover, the amount of chemicals consumed during the oxidation process will be reduced by liquid phase air oxidation at an intermediate temperature range, namely from 50° to 120° C., before the reaction is completed and then followed by liquid phase oxidation with reagent by using, for instance, nitric acid, chromic acid, hydrogen peroxide, peracetic acid, or the like.

NTCA produced by the oxidation reaction can be formed as either mono-anhydride or di-anhydride compounds, depending upon the reaction conditions, especially reaction temperature. Depending on the reaction condition, a mixture of free acid and the mono-anhydride compound will be generally formed.

Refining the NTCA can be achieved by known techniques such as acid precipitation, crystallization or extraction methods which are adapted for these compounds.

The NTCA and its anhydrides thus obtained are useful intermediates in the production of pigment and resins.

BRIEF DESCRIPTION OF THE DRAWINGS

Further objects of the invention, together with additional features and advantages accruing therefrom will be apparent from the following description and drawings in which.

DETAILED DESCRIPTION OF A PREFERRED EMBODIMENT SIDE CHAIN ALKYLATION METHOD

EXAMPLES 1 THROUGH 3

Figure 1:
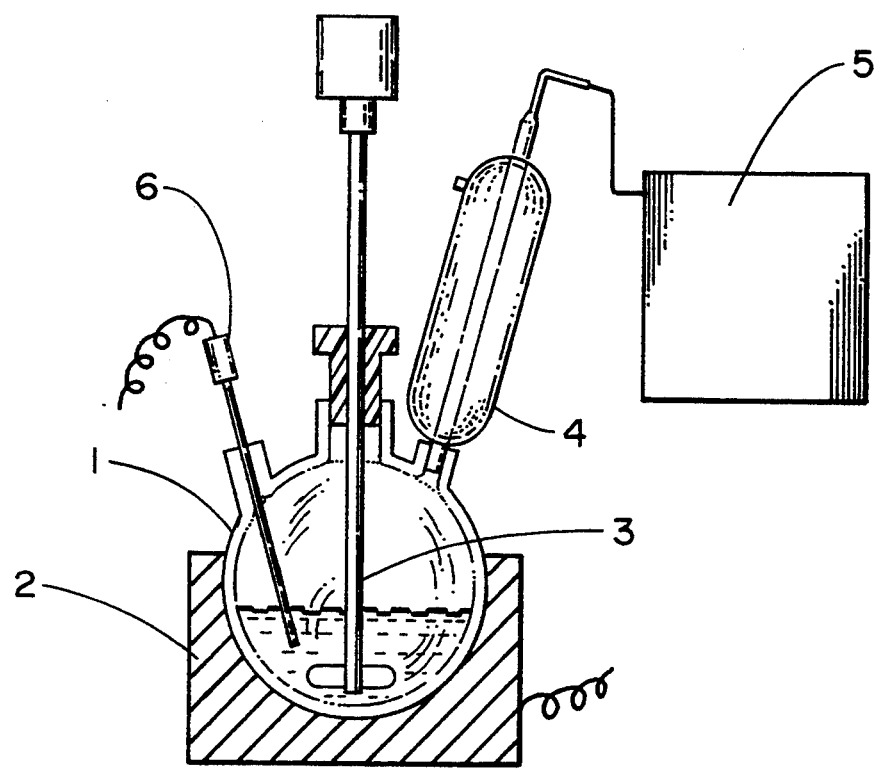
FIG. 1 is a view of an experimental apparatus employed for the dehydrogenation reaction according to the invention.

Ethyl-p-xylene 1 mol, sodium 0.020 mol and potassium 0.013 mol as an alkaline metal catalyst, and biphenyl 0.0083 mol as a promoter were introduced into a 300 ml glass flask with a stirrer, and were heated and stirred at 110° C. for 5 minutes. After cooling down to 60° C., tetrahydrofuran was added while stirring as seen in Table 1. At this temperature, 1,3-butadiene was fed at a rate of 0.1 mol/hr for 6 hours. Water was added to quench the catalysts. After separation the reaction product was analyzed by gas chromatography in terms of area percentage. The results are also listed in Table 1. The conversion is shown by the analyzed value based on reacted ethyl-p-xylene in terms of area percentage, and the selectivity indicates the area percentage of the target product (5-p-xylyl-hexene) in the butadiene adducts.

TABLE 1

| Example | Solvent (ml) | 5-(p-xylyl)-hexene Conversion (%) | Selectivity (%) |
|---|---|---|---|
| 1 | tetrahydrofuran:50 | 49.2 | 66.5 |
| 2 | tetrahydrofuran:100 | 48.2 | 72.2 |
| 3 | tetrahydrofuran:200 | 46.2 | 73.3 |

Comparison 1

A similar experiment as example 2 was proceeded under non-solvent except the reaction temperature was 120° C. for the solvent case. After quenching and separation, the reaction product was analyzed by gas chromatography. The result is listed in Table 2. The conversion is shown as the analyzed value based on reacted ethyl-p-xylene as an area percentage and the selectivity indicates the area percentage of the target product (5-p-xylene-hexene) in the butadiene adducts.

TABLE 2

| Comparison | 5-(p-xylyl)-hexene Conversion (%) | Selectivity (%) |
|---|---|---|
| 1 | 44.5 | 34.2 |

EXAMPLES 4 THROUGH 6

Ethyl-p-xylene 1 mol, alkaline metal catalysts as listed in Table 3, and biphenyl 0.0083 mol as a promoter were introduced into a 300 ml glass flask with a stirrer and were heated and kept at 110° C. while stirring for 5 minutes. After cooling down to 60° C., the tetrahydrofuran 100 ml was added and stirred. At this temperature, 1,3-butadiene was added at a rate of 0.1 mol/hr for 6 hours. The catalyst was then quenched by adding with water and reaction products were analyzed by gas chromatography after separation. The results are listed in Table 3. The conversion is shown as the analyzed value based on reacted ethyl-p-xylene as an area percentage and the selectivity indicates the area percentage of the target product (5-p-xylyl-hexene) in the butadiene adducts.

TABLE 3

| Example | Alkaline metal (mol) Na | K | Conversion (%) | Selectivity (%) |
|---|---|---|---|---|
| 4 | 0 | 0.018 | 51.2 | 69.0 |
| 5 | 0.011 | 0.007 | 46.5 | 70.8 |
| 6 | 0.018 | 0 | 45.2 | 51.8 |

EXAMPLES 7 AND 8

Similar experiments were proceeded using the procedure of example 2, except that biphenyl was used as a promoter as seen in Table 4. After quenching and separation, the reaction product was analyzed by gas chromatography. The results are seen in Talbe 4. The conversion rate is shown as the analyzed value based on reacted ethyl-p-xylene as an area percentage and the selectivity indicates the area percentage of the target product (5-p-xylyl-hexene) in the butadiene adducts.

TABLE 4

| Example | Promoter (0.8 g each) | 5-(p-xylyl)-hexene Conversion (%) | Selectivity (%) |
|---|---|---|---|
| 7 | naphthalene | 47.4 | 71.9 |
| 8 | phenanthrene | 48.3 | 64.8 |

Comparison 2

Similar experiments were proceeded as in example 2 except that the promoter was not used. After quenching and separation, the reaction product was analyzed by gas chromatography. The results are listed in Table 5. The conversion is shown as the analyzed value based on (reacted) ethyl-p-xylene as an area percentage and the selectivity indicates the area percentage of the target product (5-p-xylyl-hexene) in the butadiene adducts.

TABLE 5

| Comparison | 5-(p-xylyl)-hexene Conversion (%) | Selectivity (%) |
|---|---|---|
| 2 | 31.0 | 29.4 |

Cyclization Process 188 g of 5-(p-xylyl)-hexene and 10 g of p-toluene-sulfonic acid mono-hydride were introduced into a 300 ml glass flask. The cyclization reaction was carried out at 180° C. for 3 hours while stirring. After the reaction was completed, the reaction product was neutralized by equimoler caustic soda aqueous solution to the acid. After liquid separation, TMT 184 g was obtained. The yield was 98%.

The side chain alkylation reaction product 200 g containing 30% of 5-(p-xylyl)-hexane and p-toluene-sulfonic acid 4 g were introduced into a 300 ml glass flask. The cyclization reaction was carried out at 160° C. for 3 hours while stirring. After the reaction was completed, water was added to dissolve the p-toluene-sulfonic acid. The reaction product containing TMT was collected after liquid separation. This liquid was rectified to obtain 59.1 g of TMT. The yield was 98.5%.

The side chain alkylation reaction product 200 g containing 30% of 5-(p-xytyl)-hexane and β-naphthalene sulfonic acid 4 g were introduced into a 300 ml glass flask. The cyclization reaction was carried out at 160° C. for 3 hours. After the reaction was completed, water was added to dissolve the β-naphthalenes sulfonic acid. The reaction product containing TMT was obtained after the liquid separation. The reaction product was rectified to obtain 58.8 g of TMT. The yield was 98.0%.

The side chain alkylation reaction solution 200 g containing 30% of 5-(p-xylyl)-hexene and 4 g of 95 percent sulfuric acid 4 g were introduced into a 300 ml glass flask. The cyclization reaction was carried out at 160° C. for 3 hours while stirring. After the reaction was completed, water was added to separate the sulfuric acid and obtain the reaction product containing TMT. The reaction product was further rectified to obtain 57.3 g of TMT. The yield was 95.5%.

The side chain alkylation reaction product 200 g containing 30% of 5-(p-xylyl)-hexene and 4 g of p-toluene sulfonic acid were introduced into a 300 ml glass flask. The cyclization reaction was carried out at 100° C. for 5 hours while stirring. After the reaction was completed, water was added to separate p-toluene sulfonic acid. After the separation, the reaction product was rectified. However, TMT was not obtained.

The side chain alkylation reaction product 200 g containing 30% of 5-(p xylyl)-hexene and 4 g of phosphoric acid were introduced into a 300 ml glass flask. The cyclization reaction was proceeded at 160° C. for 3 hours while stirring. The reaction solution was added with water to separate the phosphoric acid. After separation, the reaction solution was rectified to obtain 0.4 g of TMT. The yield was 0.6%.

Dehydrogenation Process

The 50 g of TMT (cis isomer 26%, trans isomer 73%) were introduced into a 200 ml glass flask 1. The 5 g of active carbon (10% of raw material) which was supported with 3% of platinum was added. The flask was heated by the mantle heater 2 up to 250° C. for 4 hours while stirring with glass stirrer. The dehydrogenation reaction was carried out while refluxing with Liebig condenser 4. The actual reaction temperature raised from 260° C. to 285° C. by producing the dehydrogenated products. In FIG. 1, there are a rubber ballon 5 for collecting hydrogen gas and a thermometer 6.

Figure 2:
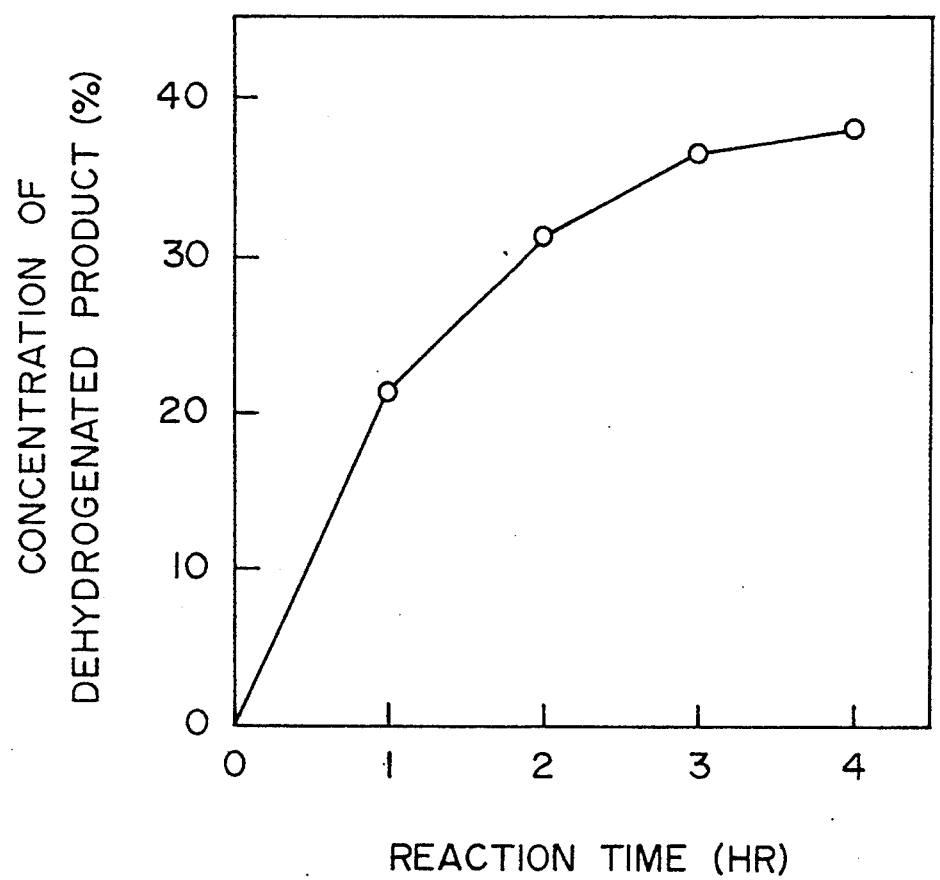
FIG. 2 shows a diagram indicating a relationship between reaction time and concentration of the reaction product during the dehydrogenation reaction according to the invention.

Changes in concentration of dehydrogenation reaction products is shown in FIG. 2.

After the dehydrogenation reaction was completed, the reaction product was filtrated to remove the catalyst at 150° C. Upon cooling to room temperature (approximately 20° C.), yellowish white crystals were precipitated. These crystals were filtered, separated, washed with ethanol 20 ml and dried to obtain dehydrogenation product 15.4 g with purity of 97.4% (1,4,5,8-tetramethylnaphthalene 36.4%, 5,6-dimethyl-1,2-dihydroacenaphthylene 61.2%).

The conversion was 37%, and the selectivity was 31.4%.

When the filtered solution, after filtering the crystals, was further subjected to the dehydrogenation process under the conditions previously described, the conversion was 35% and the selectivity was 32.7%.

Oxidation Process

Figure 3:
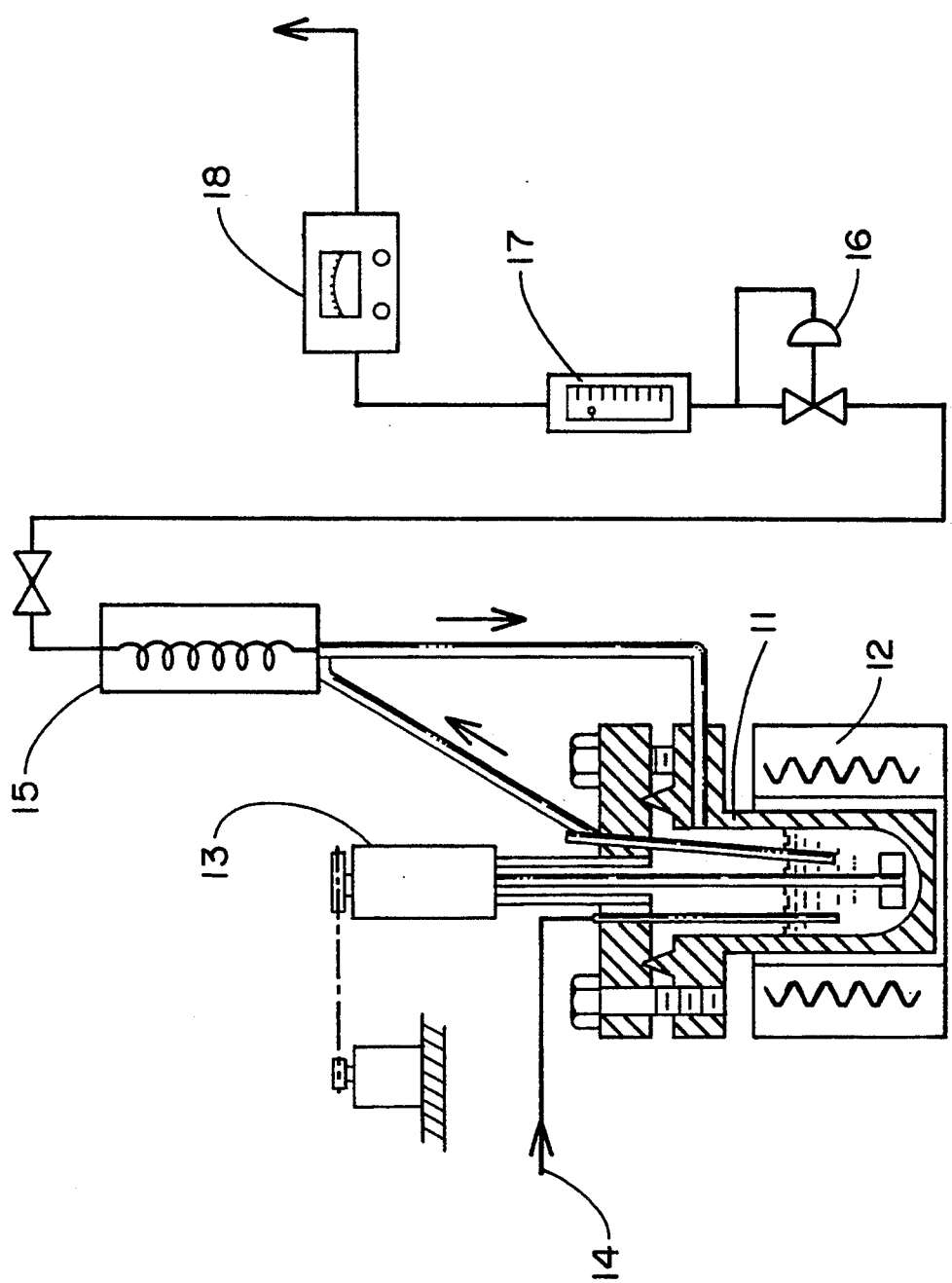
FIG. 3 is a view of the experimental apparatus used for the oxidation process according to the invention.

The oxidation raw materials 6.03 g containing 1,4,5,8-tetramethylnaphthalene 36.4% and 5,6-dimethyl-1,2-dihydroacenaphthylene 61.2%, acetic acid 300 g, cobalt acetate tetrahydride 4.11 g, manganese acetate tetrahydride 4.04 g and KBr 1.96 g (all of the last three chemicals were used as catalyst) were introduced into a 500 mol titanium autoclave 11 as eeen in FIG. 3. They were heated up to 170° C. by an electric furnace 12. The reaction pressure was 30 kg/cm$^2$G while stirring with an electromagnetic stirrer. The oxidation reaction was then carried out by feeding air for 2 hours through the air inlet tube 14 in such a way that the air flow of the exhaust gas was 3.0 l/min as converted to atmospheric pressure. In FIG. 3, there are shown a condenser 13, a pressure regulator 16, a flow meter 17 and an oxygen analyzer 18.

After the oxidation reaction was completed, yellow crystals were precipitated by cooling to room temperature. After filtering these crystals, followed by water washing and drying at 120° C. for 2 hours, 7.30 g of crystals were obtained.

After these crystals were esterized with diazomethane, they were analyzed by gas chromatography. It was found that NTCA (mono-anhydride) was formed with purity of 91.1%.

The conversion was above 99%, and the selectivity was 70.5 mol %.

As has been described above, according to the present invention, NTCA can be economically mass-produced with good yield by using inexpensive and available ethyl p-xylene, and can be supplied readily and continuously as an intermediate raw material for products such as dye, pigment, resins, or the like.

While this invention has been explained with reference to the processes described herein, it is not confined to the details as set forth and this application is intended to cover any modifications and changes as may come within the scope of the following claims.

What is claimed is:

1. A production process of 1,4,5,8-naphthalene tetracarboxylic acid comprising the steps of:
    adding 1,3-butadiene to ethyl-p-xylene in the presence of an alkaline metallic catalyst;
    subjecting 5-(p-xylyl)-hexene to a cyclization to form 1,4,5,8-tetramethyl-1,2,3,4-tetrahydronaphthalene;
    dehydrogenating the 1,4,5,8-tetramethyl-1,2,3,4-tetrahydronaphthalene at a temperature in the range of from 200° to 350° C.; and
    oxidizing a resultant product produced from the dehydrogenation.

2. The process of claim 1, wherein said step of adding 1,3-butadiene is performed in the presence of a promoter for said alkaline metal catalyst selected from the group of naphthalene, biphenyl, phenanthrene, anthracene, pyrene, and an alkyl derivatives thereof.

3. The process of claim 1, wherein said step of adding 1,3-butadiene is performed in the presence of tetrahydrofuran.

4. The process of claim 1, wherein said step of cyclizing is performed in the presence of aromatic sulfonic acid as a cyclization catalyst in a temperature range from 120° to 250° C.

5. The process of claim 1, wherein said step of dehydrogenating is performed in the presence of a palladium or platinum catalyst in a temperature range of 250° to 350° C.

6. The process of claim 1, wherein said step of oxidizing is performed by liquid phase air oxidation of 1,4,5,8-tetramethylnaphthalene in a solvent containing low molecular weight fatty acids in the presence of a heavy metal and bromine in a temperature range of 100° to 220° C.

7. A production process of 1,4,5,8-naphtha lene tetracarboxylic acid comprising the steps of:

adding 1,3-butadiene to ethyl-p-xylene in the presence of an alkaline metallic catalyst and in the presence of a promoter for said alkaline metal catalyst selected from the group of naphthalene, biphenyl, phenanthrene, anthracene, pyrene, and alkyl derivatives thereof;

subjecting 5-(p-xylyl)-hexene to a cyclization to form 1,4,5,8-tetramethyl-1,2,3,4-tetrahydronaphthalene in the presence of aromatic sulfonic acid as a cyclization catalyst in a temperature range from 120° to 250° C.;

dehydrogenating the 1,4,5,8-tetramethyl-1,2,3,4-tetrahydronaphthalene; and oxidizing a resultant product produced from the dehydrogenation.

8. The process of claim 7, wherein said step of adding 1,3-butadiene is performed in the presence of tetrahydrofuran.

9. The process of claim 8, wherein said step of dehydrogenating is performed in the presence of a palladium or platinum catalyst in a temperature range of 250° to 350° C.

10. The process of claim 8, wherein said step of oxidizing is performed by liquid phase air oxidation of 1,4,5,8-tetramethylnaphthalene in a solvent containing a low molecular weight fatty acid in the presence of a heavy metal and bromine in a temperature range of 100° to 220° C.

11. The process of claim 7, wherein said step of dehydrogenating is performed in the presence of a palladium or platinum catalyst in a temperature range of 150° to 350° C.

12. The process of claim 7, wherein said step of oxidizing is performed by liquid phase air oxidation of 1,4,5,8-tetramethylnaphthalene in a solvent containing a low molecular weight fatty acid in the presence of a heavy metal and bromine in a temperature range of 100° to 220° C.

* * * * *